United States Patent
Krüger et al.

(10) Patent No.: US 12,400,761 B2
(45) Date of Patent: Aug. 26, 2025

(54) DECISION MODULE AND METHOD FOR IMAGE-BASED OPERATIONAL DECISION SUPPORT

(71) Applicant: Siemens Healthineers AG, Forchheim (DE)

(72) Inventors: Benedikt Krüger, Ebensfeld (DE); René Kartmann, Nuremberg (DE); Peter Gall, Uttenreuth (DE)

(73) Assignee: Siemens Healthineers AG, Forchheim (DE)

( * ) Notice: Subject to any disclaimer, the term of this patent is extended or adjusted under 35 U.S.C. 154(b) by 422 days.

(21) Appl. No.: 17/939,228

(22) Filed: Sep. 7, 2022

(65) Prior Publication Data

US 2023/0072095 A1   Mar. 9, 2023

(30) Foreign Application Priority Data

Sep. 7, 2021   (EP) ..................... 21195356

(51) Int. Cl.
*G16H 50/20* (2018.01)
*G06T 7/00* (2017.01)

(52) U.S. Cl.
CPC .......... *G16H 50/20* (2018.01); *G06T 7/0012* (2013.01); *G06T 2207/20081* (2013.01); *G06T 2207/20084* (2013.01)

(58) Field of Classification Search
CPC .............................. G16H 50/20; G06T 7/0012
See application file for complete search history.

(56) References Cited

U.S. PATENT DOCUMENTS

| 6,574,304 | B1 | 6/2003 | Hsieh et al. |
| 12,148,528 | B1 * | 11/2024 | Park ................. G16H 40/67 |
| 2005/0049497 | A1 | 3/2005 | Krishnan et al. |
| 2006/0265253 | A1 | 11/2006 | Rao et al. |

(Continued)

FOREIGN PATENT DOCUMENTS

| DE | 102020212237 A1 | 3/2022 |
| EP | 3511941 A1 | 7/2019 |

(Continued)

OTHER PUBLICATIONS

Zhou J. et al.: "Graph neural networks: A review of methods and applications"; KeAi, 2020 (https://arxiv.org/ftp/arxiv/pa-pers/1812/1812.08434.pdf).

(Continued)

*Primary Examiner* — David Bilodeau
(74) *Attorney, Agent, or Firm* — Banner & Witcoff Ltd.

(57) ABSTRACT

Techniques are described for providing image-based operational decision support. The technique includes using a decision engine configured to generate output data based on a determined number of clinical findings in medical images of a patient. The decision module is configured to generate decision data depending on position data defining an actual position of the patient in a predefined clinical guideline, which comprises a set of possible next steps subsequent to the actual position. The decision data comprises information indicating which next steps from the set of possible next steps of the clinical guideline should be performed. The disclosure further describes a related method, a clinical decision system, and a related medical imaging system.

19 Claims, 4 Drawing Sheets

(56) References Cited

U.S. PATENT DOCUMENTS

| | | | | |
|---|---|---|---|---|
| 2014/0356833 | A1* | 12/2014 | Sabczynski | G16H 50/50 |
| | | | | 434/262 |
| 2015/0046176 | A1* | 2/2015 | Xu | G16H 40/20 |
| | | | | 705/2 |
| 2018/0089385 | A1* | 3/2018 | Gupta | G16H 70/60 |
| 2019/0221304 | A1* | 7/2019 | Ionasec | G16H 15/00 |
| 2019/0228857 | A1 | 7/2019 | Lin et al. | |
| 2019/0354882 | A1* | 11/2019 | Sharma | G16H 30/20 |
| 2020/0365267 | A1 | 11/2020 | Lauer | |
| 2021/0098135 | A1 | 4/2021 | Frings et al. | |
| 2021/0118554 | A1 | 4/2021 | Amthor et al. | |
| 2021/0406731 | A1* | 12/2021 | Keren | G16B 20/00 |
| 2021/0407694 | A1 | 12/2021 | Deckert et al. | |
| 2022/0101959 | A1 | 3/2022 | Vallines et al. | |
| 2022/0180447 | A1* | 6/2022 | Kearney | G06N 3/047 |
| 2022/0215961 | A1* | 7/2022 | Jacobs | G16H 50/70 |
| 2022/0392065 | A1* | 12/2022 | Min | A61B 8/0883 |
| 2024/0194323 | A1* | 6/2024 | Arrowsmith | A61B 6/463 |

FOREIGN PATENT DOCUMENTS

| | | |
|---|---|---|
| EP | 3599611 A1 | 1/2020 |
| EP | 3637424 A1 | 4/2020 |
| EP | 3745416 A1 | 12/2020 |
| EP | 3799074 A1 | 3/2021 |
| EP | 3837693 A1 | 6/2021 |
| WO | 2009050676 A1 | 4/2009 |

OTHER PUBLICATIONS

"Clinical Practice Guidelines", National Center for complementary and Integrative Health, 2015, https://www.nccih.nih.gov/health/providers/clinicalpractice.

* cited by examiner

DECISION MODULE AND METHOD FOR IMAGE-BASED OPERATIONAL DECISION SUPPORT

CROSS-REFERENCE TO RELATED APPLICATIONS

The present application claims the benefit of the filing date of Europe patent application no. EP 21195356.7, filed on Sep. 7, 2021, the contents of which are incorporated herein by reference in their entirety.

TECHNICAL FIELD

The disclosure describes a decision module, a method, and a clinical decision system for image-based operational decision support. The disclosure describes a method and a device for controlling a medical imaging system, e.g., a magnetic resonance imaging system or a computed tomography system. The disclosure combines image-based operational decision support and clinical pathways.

BACKGROUND

In medicine, there is often a sequence of diagnostic steps for certain medical conditions, e.g., illnesses. Regarding an examination to be performed, this examination may strongly depend on a finding or a result of a previous imaging diagnosis. For example, a diagnostic mammography is only carried out after a mammography screening with a suspicious finding, or a chest CT is performed after an X-ray examination of the chest with a suspicious finding.

Especially in medical imaging, often a sequence of medical imaging scans can be necessary to accurately diagnose a certain medical condition of a patient. In the sequence of medical imaging scans, typically the performance of a certain kind of medical imaging scan is based on the results of a previously-performed medical imaging scan.

For example, an MRI scan of the abdomen region may lead to incidental findings of suspicious lesions in the liver of the patient, which leads to the necessity of a follow-up MRI scan focused on the liver of the patient, potentially employing special MRI techniques to be able to generate liver images (e.g., DIXON-imaging, zoomed imaging, special motion compensation techniques, etc.). As a further example, the results of the MRI scan might turn out to be insufficient to diagnose a certain condition of the patient, so that the MRI scan needs to be repeated with different imaging conditions, e.g. employing different kind of MRI imaging sequences or the injection of a contrast agent.

SUMMARY

Up to now, there is the possibility to aid examinations with an automated diagnosis.

For instance, U.S. Pat. No. 6,574,304 B1 describes processing first imaging data from a first imaging system with a computer-aided diagnosis (CAD) algorithm and acquiring second imaging data based upon the results of the CAD algorithm to enable a complete useful set of information to be gathered during a single patient session. The subsequent acquisition may include acquisition of data from other regions of the patient's body, at different orientations with respect to tissues of interest, at different resolution levels, and so forth.

WO 2009/050676 A1 describes an MRI imaging method comprising the acquisition of a first image and the identification of a suspected pathology based on the first image. Based on the suspected pathology, an MRI session comprising a suitable pulse sequence, slice orientation, or further imaging parameter is planned.

US 2020/0365267 A1 describes a decentrally-controlled imaging-based patient data extraction method including e.g., a checking process as to whether image quality is adequate and, if not, to perform a renewed MR image recording with adjusted parameters, e.g., usage of contrast medium. The usage of neural networks is suggested in this document.

US 2019/0228857 A1 describes a method for smart image protocolling, especially with regard to MR imaging. Disease features are extracted from a set of medical images and, based on the extracted disease features, a machine learning trained algorithm determines if the imaging goal is achieved for the patient. If the desired medical imaging goal has not been achieved, the machine learning trained algorithm is used to select a second medical imaging sequence.

Typically, images produced in a first medical imaging scan have to be assessed, e.g. by a radiologist, to prescribe the follow-up scan of the patient. This might lead to several disadvantages:

A time delay between the first medical imaging scan and the follow-up scan leading to a delay in providing the correct diagnosis of the patient and a delay in the start of the treatment;

organizational burden and further costs as a follow-up scan of the patient needs to be scheduled and performed (including the necessity to perform again a time-consuming preparation of the patient for the follow-up scan); and patient dissatisfaction.

Conventionally, the clinical context of the patient is not taken into account, but only the patient imaging data. So known procedures and systems do not leverage the full information available for a certain patient.

It is the object of the present disclosure to improve the known systems, devices, and methods to facilitate an improvement in image-based operational decision support, especially in controlling a medical imaging system.

This object is achieved by the embodiments described herein, including the claims.

The present disclosure describes an implementation of a "test-algorithm chain in medical imaging" with a particular focus on a specific implementation for magnetic resonance imaging (MRI). Of course, the described framework can also be applied in other forms of diagnostic imaging, e.g., computed tomography (CT), X-ray imaging, positron emission tomography (PET), single-photon emission computed tomography (SPECT), ultrasound, molecular imaging, or other suitable medical imaging procedures.

A decision module according to the disclosure for image-based operational decision support comprises a decision engine that is configured to generate output data based on a determined number of clinical findings in medical images of a patient. This decision module, e.g. the decision engine, is configured to generate decision data depending on position data defining an actual position of the patient in a clinical guideline or "clinical pathway" (and the determined number of clinical findings or the output data). The clinical guideline comprises a set of possible next steps that follow subsequent to the actual position, and the resulting decision data comprises information indicating which next steps from this set of possible next steps of the clinical guideline should be performed. The decision data comprises at least a decision whether a further imaging examination or other type of diagnostic test is necessary or not.

A method according to the disclosure for image-based operational decision support comprises:

provoking initial (medical) imaging data from a preceding examination of a patient;

determining a number of clinical findings by automated processing of the initial imaging data and/or computer aided diagnosis;

providing position data defining a position of the patient in a predefined clinical guideline;

generating decision data based on the determined number of clinical findings, the position data, and the structure of the clinical guideline, with a decision module according to the disclosure, wherein the clinical guideline comprises a set of possible next steps subsequent to the actual position and the decision data at least comprises an information indicating which next steps from the set of possible next steps of the clinical guideline should be performed; and outputting the decision data.

A clinical decision system according to the disclosure for image-based operational decision support, comprises:

a data interface configured to receive initial imaging data from a preceding examination of a patient, and position data defining a position of the patient in a predefined clinical guideline;

a CAD engine configured to determine a number of clinical findings by automated processing of the initial imaging data;

a decision module according to the disclosure, configured to generate decision data based on the determined number of clinical findings, the provided position, and the structure of the clinical guideline; and a data interface configured to output the decision data.

The general idea is to use results of a tool like the AI-Rad Companion, an AI-based system that calculates measurements, and/or diagnosis based on medical imaging data, to (automatically) order a further exam. Clinical decision support systems guiding the scan or examination workflow while the patient is still positioned in the scanner, or at least shortly after the patient leaves the scanner, can lead to very efficient and result-oriented scanning also in the diagnostic imaging arena. The underlying general workflow would be that the AI-Rad Companion or a similar tool receives an imaging exam result (of whatever modality, e.g., a DICOM image), recommends what to do next, and enables a so-called "test-algorithm chain" in imaging. The output of data (decision data or possibly additional data) serves the acquisition of additional images and, thus, the control of a medical imaging system.

The problem that is addressed by this disclosure is to use additional information from clinical guidelines (e.g., standard operating procedures of a healthcare provider, or a standardized clinical guideline of a standardization body) to automatically provide or restrict a possible solution space for a further step after a certain initial finding.

The general structure as described herein forms the basis for above method and clinical decision system without the additional guideline input.

At first, a patient undergoes a first medical imaging examination. This examination could e.g. be a computed tomography (CT), a magnetic resonance imaging (MRI), an X-ray imaging, positron emission tomography (PET), single-photon emission computed tomography (SPECT), ultrasound, etc., related to a specific medical question.

Suitable imaging data for the disclosure may comprise all types of digital medical images, e.g. X-ray images, CT-images, MR-images, etc. Regarding the images, it could be advantageous for easily understanding the disclosure to imagine the preferred case in which the images are scans of a patient and the parameters are scan parameters.

The initial imaging data is, e.g. a number of digital images from a preceding scan of a patient. This initial imaging data may be retrieved from a database. However, it could be advantageous to apply the method right at the time of the examination and/or directly at the respective imaging modality. Then, the step of providing initial imaging data may e.g. be split into the following sub-sets:

providing a first set of imaging parameter values, e.g. by a semi-automatic or automatic process; and recording an image based on the initial set of imaging parameter values, wherein the resulting initial imaging data is provided for the determination of clinical findings and e.g. also for the generation of the set of imaging parameter values.

The initial set of imaging parameter values may be set by known manual processes, e.g. by using a control console of a medical imaging system, semi-automatic processes (e.g., by a user selecting from and/or confirming a suggestion of the medical imaging system, wherein the suggestion is determined based on input data comprising patient data and/or referral data) or automatic processes (e.g. by the system automatically determining the initial set of imaging parameter values by the medical imaging system or a control device based on input data comprising patient data and/or referral data). The initial set of imaging parameter values may e.g. form a complete set of values for all scan parameters needed for performing a first scan with a medical imaging system. Therefore, the initial set of imaging parameter values may e.g. be adapted for generation of medical images suitable for assessing the specific medical condition, which the prescription for the first scan with the medical imaging system is based.

The initial set of imaging parameter values is then used for the first scan with the medical imaging system. In addition, the initial set of imaging parameter values can optionally be used as an input for the decision engine.

Based on the received initial set of imaging parameter values, a first scan of the patient is performed with the medical imaging system producing the initial medical imaging data. The initial medical imaging data may be suitable for assessing the specific medical condition, which the prescription for the first scan with the medical imaging system is based.

After the initial imaging data is provided, the resulting initial imaging data from the first examination is provided to an image processing system, the image processing system e.g. based on machine learning (ML) and/or on artificial intelligence (AI), e.g. the AI-Rad Companion. This AI/ML-based image processing system is designated here with the expression "CAD engine" (CAD: "computer aided diagnostics") and may be located on premises or outside of the hospital, e.g., in a cloud offering. The initial imaging data is received by a data interface and provided for the method.

The CAD engine receives the initial medical imaging data, processes them, and generates a number of clinical findings based on the initial medical imaging data. The number of clinical findings are later used as an input for the decision engine.

The clinical finding may be e.g. a diagnosis, a structured report, another image (e.g., a segmentation of the input image), measurements related to certain structures within the initial medical imaging data, etc. Additionally or alternatively, the number of clinical findings may comprise a measure for the quality or the reliability of the diagnosis (e.g., a number between 0 and 1 indicating how sure a certain finding is). A user may e.g. have a manual possibility to verify the number of clinical findings, e.g. by accepting or rejecting the number of clinical findings before the further processing of the number of clinical findings. This has the advantage that possible errors due to automatic processing can be reduced.

In an embodiment, the CAD engine includes an automatic processing algorithm receiving the initial medical imaging data as input data and producing the number of clinical findings as output data. Such a CAD engine in generally known in the art. A CAD engine may e.g. include appropriate pre-processing algorithms applied on the initial medical imaging data (e.g., segmentation, landmark detection, registration, etc.). Another example CAD engine comprises the usage of a reference atlas to process the initial medical imaging data (e.g., in case of brain MRI input data) to generate the number of clinical findings. Another example CAD engine comprises one or more suitable (deep) neural network(s), e.g. convolutional neural network(s), applied on the initial medical imaging data as input data to generate the number of clinical findings.

Clinical findings generated by the CAD engine may e.g. comprise one item or a combination of the items of the following list:
- a binary indication whether the patient is afflicted with a certain medical condition or not;
- an indication with which medical condition(s) the patient is afflicted with (including incidental findings not connected to specific medical condition to be assessed by the CAD engine);
- a probability (e.g., percentage value or other suitable indication that the patient is afflicted with a certain medical condition;
- a (numerical) indication about the severity of the affliction of the patient with a certain medical condition;
- an indication regarding the stage/staging of a certain disease which the patient is afflicted;
- spatially-resolved localization data.

The spatially-resolved localization data may e.g. be saved in a suitable data format, e.g. the DICOM format and may include e.g. one or more of the following information:
- a spatial distribution of the (severity of the) affliction of the patient with a certain medical condition;
- the position(s) of suspicious finding(s) (e.g., lesion, nodule, abnormality) in the initial medical imaging data;
- a segmentation of the initial medical imaging data. Such segmentation can e.g., include a segmented region in the initial medical imaging data, being an area containing features indicating the affliction of the patient with a certain medical condition;
- certain (sets of) coordinates in the initial medical imaging data;
- a segmentation map having the same or a lower resolution than the first medical imaging data;
- spatially-resolved numerical values in the same or a lower resolution than the initial medical imaging data.

After that, the number of clinical findings is used as input to the decision engine that can also comprise an AI/ML algorithm. The decision engine may be part of the same system as the CAD engine, or both can be related to different systems. The decision engine may be an offering on-premises or a as part of a cloud-based computing system.

The decision engine takes the number of clinical findings generated by the above described CAD engine as inputs, processes them, and presents a decision as output to the parameter setting engine (decision data). Generally, the decision engine is configured to generate a decision whether a further recording of a number of images, e.g., a follow-up scan, is needed or advantageous based on the number of clinical findings. Furthermore, the decision engine may be configured to generate a decision based on the number of clinical findings, what kind of diagnostic goal should be pursued by the follow-up scan, i.e., which medical condition, which is suspected based on the number of clinical findings, should be the target of the follow-up scan.

In case the input data (i.e., the number of clinical findings and maybe further data) comprise a binary indication whether the patient is afflicted with a certain medical condition or not, the decision engine may work with existing lookup tables to determine if follow-up scans should be appropriate in case the affliction with the medical condition is indicated. Furthermore, the lookup tables can contain the respective diagnostic goals which should be pursued by the follow-up scan.

In case the follow-up scan is to be performed using the same medical imaging modality that was already used for the first scan, the decision engine may e.g. base its decisions on such medical conditions, which can be appropriately diagnosed using this imaging modality (i.e. in this case the lookup tables should be restricted to the respective diagnostic goals that can be achieved using exactly this imaging modality).

In case the input data (i.e., the number of clinical findings) comprise a more complex structure, e.g. a set of numerical values or the above-described spatially-resolved localization data, the decision engine should employ more sophisticated processing means, e.g. the processing of the number of clinical findings to generate the decision can employ a trained (deep) neural network.

In general, a decision engine is generally known. The disclosure may be considered independent from the architecture of the decision engine. In the decision module, a well-known decision engine may be used wherein its output is modified according to the disclosure or a specially trained and/or structured decision engine could be used, wherein the training was specially drawn to produce the desired output. An example decision engine may comprise ML-networks for the inputs (clinical findings and e.g., additional patient data) and comprise a plurality of fully connected layers to combine the outputs of the ML-networks to produce decision data.

An example (deep) neural network can have the clinical findings assigned to respective input nodes and the decision assigned to respective output nodes. In case the clinical findings comprise (a set of) numerical values, the number of input nodes of the neural network can correspond to the number of numerical values and each of the input nodes can be assigned one of the numerical values. In case the clinical findings comprise spatially-resolved localization data (i.e., the clinical findings can be regarded as image data), the spatially-resolved localization data can be fed into a corresponding number of input nodes of the neural network.

In an embodiment, the neural network produces the decision at its respective output node(s):
- in case the decision is embodied as a binary decision, whether a follow-up scan is needed or advantageous based on the number of clinical findings, the binary decision can be presented at a single binary output node of the neural network;
- in case the decision comprises a selection of a specific follow-up scan which is needed or advantageous based on the clinical finding, the corresponding selection can be presented at one or multiple output nodes of the neural network;

in case the decision comprises an indication, what kind of diagnostic goal should be pursued by the follow-up scan, i.e., which medical condition, which is suspected based on the number of clinical findings, should be the target of the follow-up scan, the output nodes of the neural network can have a more complex structure.

Generating data in which the decision engine classifier can originate its work may be implemented on e.g. two types of training. Both types described in the following can also be combined.

The first example for training of the decision engine classifier, e.g., the training of the neural network is based on an analysis of previously-performed imaging studies (with a follow-up scan performed and without a follow-up scan performed). Additionally, also the parameters of the follow-up scan can be used (indicating what kind of diagnostic goal was pursued by the follow-up scan), and data related to the first scan and the follow-up scan can be reported. In this case, imaging studies comprising a follow-up scan may e.g. correspond to training data of a first category (i.e., "follow-up scan needed") and imaging studies not comprising a follow-up scan correspond to training data of a second category (i.e., "no follow-up scan needed"). Based on the training data in the first category and the second category, the classifier contained by the decision engine, e.g., the neural network, can be trained. Such training data can be generated based on a monitoring of the performance of several imaging studies on different medical imaging machines, e.g., employing the "Virtual Cockpit" technology. Such data can be transferred from the medical imaging machines via a network to the servers of the providers of the methods as described herein. Therefore, it is possible that also rare and complex diagnostic questions can be assessed by the decision engine based on "human scan coaches," which the decision engine learns from (on a business perspective: one can also assess the usage frequency of different use cases to assess which use cases should be automated first). By this method, training data can be generated for the decision engine without having to perform a manual annotation.

The second example to generate data which the decision engine classifier can base its work on the following method: Based on the initial medical imaging data and the number of clinical findings (e.g., of a CAD engine), a location of the patient in a certain clinical pathway is determined, wherein the training on the decision engine should be based on the whole path of a patient through a clinical guideline (i.e., completed patients). This means that if a certain node corresponds to the first imaging examination, the ground truth next step would be the actual step taken by the patient following the pathway, and not the possible result space. Accordingly, a suitable follow-up scan is determined based on the current location of the patient in the clinical pathway and an analysis of linked nodes in the clinical pathway (e.g. supported by the AI Pathway Companion).

Generally, the output of a decision engine comprises at least information whether a further imaging examination is necessary or not. Instead of a further imaging examination, other types of diagnostic tests (e.g., laboratory tests etc.) can be used. The further imaging examination can be necessary e.g. due to three reasons:

A. The dependence on the outcome of the first examination, e.g., if a tumor did not grow, a follow up in some month will be the decision, but of the tumor did grow, the decision will be that a more detailed examination will be necessary (now), B. The first imaging examination was not able to answer the posed diagnostic question for certain (example: the first imaging examination was an X-ray scan to determine the presence of possible lung nodules, that did not have a result beyond doubt, so a second imaging examination using a computed tomography apparatus needs to be scheduled); and C. The first imaging examination resulted in an accidental finding (unrelated to the diagnostic purpose of the first imaging examination) that needs a confirmation or a quantification by another imaging examination.

It should be noted that concerning new findings, an appropriate clinical guideline could be used. Depending on the presence of the clinical guideline to the method, there are certain possibilities. For example, in the case that the guideline or a part, i.e. the next steps, is present in the position data (location plus the next possible steps), there is no issue. In the case that the clinical guideline is present in a memory, this guideline may contain a vast number of possibilities, or the memory may comprise several guidelines for different diseases. Since the essence of the embodiments of the disclosure is that the resulting decision data should only comprise a decision between the next possible steps from a given location in the clinical pathway, it is only important to clarify which steps are the next possible steps for any location and a present clinical finding.

Thus, due to the incidental finding, the position of the patient in the clinical guideline may change (in this guideline or between different guidelines). For example, in a situation where a single tumor is suspected within the patient, but the first imaging exam already reveals that there are metastasizes, the patient could suddenly be located at a very different point of the clinical guidelines (because a later stage of cancer has to be diagnosed or treated different than an earlier stage of cancer). Alternatively, due to the incidental finding, another guideline could be taken into account. For example, after an X-Ray exam of the chest to check for pneumonia with a finding of lung nodules, the clinical guideline for the incidental finding will become relevant.

Concerning the decision module, as indicated above, the decision module may also implement position data in contrast to a normal decision engine. this is explained further below. However, in any case, decision data is produced.

The decision data is then outputted. This may result in a further imaging examination of the patient or a diagnostic exam of any other kind, e.g. in a laboratory. One advantage of this procedure is that decision data may be present very fast. Thus, in the case the decision data indicates that the modality for the first and the second imaging examination could be the same, the further imaging examination can be executed directly after the first imaging examination (e.g., subsequent to a first scan), without the patient leaving the imaging modality. For example, the further imaging examination can be defined by another protocol sequence to be executed during or after a predefined protocol sequence, e.g. due to diagnostic uncertainty or due to incidental clinical findings.

The decision module differs from known decision engines since the decision module is configured to generate a decision based on the location of the patient in the clinical guideline, wherein the location is given by the "position data." It should be noted that both should be known, i.e. the clinical guideline (at least the steps following from the location of the patient) and the location of the patient in this clinical guideline. This could be realized in that the decision module has access to data comprising information about the complete clinical guideline, in adding the relevant information to the position data, or in training a decision engine on the complete clinical guideline and (all) possible locations of the patient.

Concerning the decision module, the decision module may comprise a decision engine that is trained to process a position in a clinical guideline. Such decision engine may e.g. additionally comprise a graph neural network configured to process the inputted position data. A graph neural network is a network that can process mathematical graphs as input. In this case, the input could e.g. be a labeled graph (representing the respective clinical guideline) with a special label (e.g., "1") at the node the patient was located, and a special other label (e.g., "0") at all other nodes. This is e.g., known from Jie Zhou et al. "Graph neural networks: A review of methods and applications"; KeAi, 2020 (https://arxiv.org/ftp/arxiv/papers/1812/1812.08434.pdf).

To generate training and test data for such a decision module (e.g. the decision engine), embodiments include the use of completed clinical pathways of patients in clinical guidelines. For instance, for a certain point within the clinical guideline, whether and which a second diagnostic examination has been used on a certain patient may be used as a ground truth for the decision engine. By restricting the training data to a certain hospital or a certain set of hospitals, it is possible to also learn based on SOP (standard operating procedures) for the single hospital and/or the set of hospitals. Alternatively or additionally, a user may manually label locations in a clinical guideline with suggestions for clinical pathways for training (image) data of patients.

The decision module may also comprise several decision engines that have been trained for producing decision data for a number of special nodes of a clinical guideline, and the decision module comprises a selection module that is designed to choose the matching decision engine for the node, the patient is located.

The decision module may also comprise one decision engine of a known configuration and a guideline module configured to generate decision data by selecting the output data of the decision engine depending on the position data and the next steps of the clinical guideline from the actual position of the patient. The clinical guideline comprises a set of possible next steps subsequent to the actual position of the patient.

Nevertheless, the output of the CAD engine is then processed by a decision engine of the decision module, and the output of the decision module (the decision data) comprises an information (e.g., a decision score), indicating which next steps from a set of possible next steps of the clinical guideline should be performed.

A "clinical guideline" or a "clinical pathway" may be represented as directed graph comprising nodes and directed edges between the nodes. For instance, a clinical guideline comprises one (e.g. exactly one) origin node and at least final nodes, wherein the origin node represents a patient and/or its diagnosis and treatment starting to follow the respective guideline, and wherein the final node indicates the final step before the patient and/or its diagnosis and treatment stop to follow the respective guideline. A node in the clinical guideline can correspond to a certain diagnostic step or a certain treatment of the patient, or can be a decision node. Nodes that are connected by a directed edge correspond to possible following steps (possible treatment recommendations, or additional diagnostic steps) for the previous step. Note that edges can also correspond to certain steps to be executed, however, it is always possible to replace such an edge with a node corresponding to said step with one (e.g. exactly one) incoming and one outgoing empty edge. In general, a clinical guideline is defined by a standardization body and is valid for a plurality of organizations (i.e., a whole country). In contrast, a standard operating procedure is adapted to the specific needs or the specific processes of a certain institution, and can be based on a clinical guideline of a standardization body. For instance, a standard operating procedure is a certain kind of a clinical guideline. Within this application, the terms "clinical guideline," "clinical pathway" and "standard operating procedure," may be exchanged without modifying the underlying concept of the disclosure. As said above, the disclosure does not necessarily need a complete clinical guideline, but at least a directed graph representing at least a part of a medical guideline comprising the node where the patient is located. Concerning a clinical guideline, document EP 3837693 A1 or https://www.nccih.nih.gov/health/providers/clinicalpractice render additional information and possible definitions.

Locating patients in clinical guidelines as well as creating standard operating procedures based on deviations from guidelines is known in the art, and is e.g., described in EP 3637424 A1. For instance, for locating a patient in the guideline, the available patient data (potentially from a plurality of different IT systems within a hospital, e.g., form a hospital information system, HIS, a laboratory information system, LIS, a radiology information system, RIS, and/or an electronic medical record, EMR, etc.) has to be correlated with the possible steps within the guidelines. For example, if the patient data indicates that a certain step of the guideline has already been performed, or the result (e.g., a diagnostic value) of this certain step of the guideline is already present in the patient data, the patient is to be located after the certain step of the guideline, and vice versa. For instance, the patient can be located at the last performed step in a sequence of performed steps according to the guideline. Alternatively, for each step in the guideline a probability value can be calculated based on whether previous steps and subsequent steps have been executed according to the patient data, and the step with an extremal probability can be selected.

Thus, the minimum information needed by the disclosure is the location of the patient (given in the position data), and a number of possible next steps for the patient based on the position of the patient, wherein this number should be greater than one to have the need for a decision. At least one of the possible next steps should refer to a further imaging examination or another type of diagnostic tests e.g., a laboratory test.

The decision data then comprises a number of these next steps as information. This number may be one in the case that only one possibility is desired as output. However, the number may also be larger in the case where there is a plurality of next steps and individual decision scores for these steps are preferred in the information. Thus, the decision module provides information indicating which next steps from a set of possible next steps of the clinical guideline originating from the actual position (e.g. current position) of the patient should be performed.

As already said above, the decision data may be generated by the decision module in different ways:
    by using a specially trained decision engine;
    by using a (possibly known) decision engine and a guideline module; or by using several (possibly known) decision engines and a selection module.

These possibilities may also be combined. For example, the selection module may select (depending on the position data), whether the specially trained decision engine should be used or the output data should be post processed by the guideline module.

A control device according to the disclosure for controlling a medical imaging system comprises a clinical decision system according to the disclosure. Alternatively or additionally, the control device is configured to perform the method according to the disclosure. The control device may comprise additional units or devices for controlling components of a medical imaging system.

A medical imaging system according to the disclosure for recording images of a patient in form of imaging data comprises a decision module according to the disclosure and e.g. a clinical decision system according to the disclosure. In an embodiment, the medical imaging system comprises a control device according to the disclosure. The medical imaging system may be configured for performing magnetic resonance imaging (MRI), computed tomography (CT), X-ray imaging, positron emission tomography (PET), single-photon emission computed tomography (SPECT), ultrasound, molecular imaging, or any other suitable medical imaging procedures.

Some units or modules of the disclosure mentioned above can be completely or partially realized as software modules (e.g. computer-readable and/or executable instructions) running on and/or being configured to be executed by a processor of a computing system (e.g., a control device). A realization largely in the form of software can have the advantage that applications already installed on an existing system can be updated, with relatively little effort, to install and run these units of the present application. The object of the disclosure is also achieved by a computer program product with a computer program that is directly loadable into the memory of a computing system, and which comprises program units to perform the steps of the inventive method when the program is executed by the computing system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a computing system. A processor unit can comprise one or more microprocessors or processing circuitry, or their equivalents.

Particularly advantageous embodiments and features of the disclosure are described herein, including the claims, as revealed in the following description. Features of different claim categories may be combined as appropriate to give further embodiments not described herein.

It is assumed that x denotes initial imaging data from the first imaging examination, e.g., a medical image in the DICOM format. This initial imaging data x is used as the input to an AI/ML based image processing denoted by the function ML with the result y=ML(x), wherein y denotes the image-based clinical findings.

The clinical findings y can be a single number (e.g., representing a disease) or a set of numbers (e.g., between 0 and 1 for indicating the probability for a number of certain diseases, or a certain geometrical measurement within the body). Furthermore, y may represent a structured report or even again a medical image (e.g., a segmentation of the input image x). Also, other data or combinations of those data can be used.

The decision engine can now provide a function D that takes as input at least the image-based clinical findings y and selects from a set of potential second diagnostic examinations: e=D(y) with e∈{$e_0, e_1, e_2, \ldots$}

The decision engine can also take as input additional patient data p: e=D(y, p) with e∈{$e_0, e_1, e_2, \ldots$}

Here, {$e_0, e_1, e_2, \ldots$} is the set of second diagnostic examinations. The element $e_0$ can be considered as special "next action," namely that no further diagnostic examination is necessary. The other elements ($e_1, e_2, \ldots$) comprise for example the modality that needs to be used for the certain second diagnostic examination (e.g., MR, CT, X-Ray, PET, SPECT, diagnostic based on a certain body fluid, like blood diagnostic or liquor diagnostic, etc.) and a protocol that needs to be followed by the examination (e.g., body region to be imaged, imaging protocol to be used, pulse sequence to be used, contrast agent to be used, values to be derived from a certain laboratory test, etc.).

A decision module in accordance with an embodiment comprises a decision engine that has been trained on determined clinical findings and position data to generate decision data as output data. Since this embodiment uses a specially trained decision engine, the output data now comprises information indicating which next steps from a set of possible next steps of the clinical guideline subsequent to the actual position of the patient should be performed. This output data could directly be used as decision data, theoretically without any post-processing step. Such a decision engine has been described above.

Thus, the current position of the patient in the guidelines is used as additional input variable for the decision engine D: e=D(y, p, pos) or =D(y, p(pos)) with e∈{$e_0, e_1, e_2, \ldots$}.

Here, the variable pos indicates the position of the patient in the guideline and represents the position data. For instance, this variable may take values from a discrete set of potential positions in the guidelines (e.g., a node element in the guidelines, an integer variable or a string variable).

Another possibility is to use the current position of the patient in the guidelines for post-processing the results of the decision engine. A decision module in accordance with an embodiment comprises a guideline module configured to perform post-processing the output data of the decision engine and to generate decision data by selecting the output data depending on the position data and the next steps of the clinical guideline from the actual position of the patient. The guideline module may comprise e.g. a trained module that has been trained on multiple sets of output data of a decision engine, a number of predefined clinical guidelines, and position data of a training patient to generate decision data, wherein a ground truth within the training comprises information indicating which next step from a set of possible next steps of a clinical guideline subsequent to an actual position indicated by the position data the training patient was undergoing.

For example, the output of the decision engine may be a vector e of probabilities: e=D(y, p) with e∈$[0, 1]^{E+1}$.

Here, $e_0 \in [0, 1]$ represents the probability that no second examination needs to be done, and every entry $e_i \in [0, 1]$ corresponds to the probability for a certain second diagnostic exam $e_i$. The integer E represents the number of possible second diagnostic examinations $e_i$ and the resulting dimension represents the number of examinations plus the one probability that no second examination needs to be done.

The position of the patient within the guidelines defines a set of possible second diagnostic examinations, which is a subset of all further possibilities $\{e_0, e_1, e_2, \ldots\}$. This can be encoded in a vector $d \in \{0, 1\}^{E+1}$ wherein $d_0 \in \{0, 1\}$ indicates whether there is the possibility to have no second diagnostic exam ($d_0=1$), or not ($d_0=0$), and wherein $d_i \in \{0, 1\}$ indicates whether there is the possibility (according to the guidelines) to have a second diagnostic exam $e_i$ ($d_i=1$) or not ($d_i=0$).

The result e' (e.g., a corrected vector) can then be calculated based on a point product with a component-wise multiplication $e_i' = e_i \cdot d_i$, and the result e' can be used to determine the next step (e.g., based on the entry with the maximal value).

The guideline engine comprises the function d and is configured to calculate the remaining possibilities e' on the basis of d.

Thus, d could e.g. be understood as a mask, remaining only the possibilities from the location in the clinical guideline. The guideline engine may produce one single result (the decision for a single possibility of the possible steps) or a vector with an indicator for the decision (a single entry in the vector).

In a more complex scenario, the vector e' could provide non-integer scores (e.g. probabilities) for every entry of e'.

A decision module in an embodiment comprises a selection module configured to select a decision engine from a number of trained decision engines based on the position data.

In an embodiment, each of the trained decision engines has been trained based on training data, wherein the training data comprises a determined number of clinical findings of a training patient and a ground truth comprising information indicating which next step from a set of possible next steps of a clinical guideline subsequent to an actual position indicated by the position data the training patient was undergoing, to generate decision data as output data. Such selection module may e.g. comprise a mapping function, e.g., a table, assigning individual decision engines to possible locations in the clinical guideline.

A decision module in an embodiment is configured to generate decision data also depending on predefined additional patient data, e.g. the age, weight, size, and the sex of the patient, health condition, known co-morbidities, laboratory results and/or prior imaging results, etc. This can be achieved by training the decision engine also on this data.

A decision module in an embodiment is configured to additionally generate information about a modality to be used for a further imaging examination, about which imaging protocol to be used or about scheduling a further imaging examination.

A in an embodiment is configured to additionally output a suggested set of imaging parameter values for recording a number of images of the patient in the course of a further imaging examination. Based on the number of clinical findings, the decision data and the suggested set of imaging parameter values are generated. The expression "suggested" means that the set of imaging parameter values is generated automatically and may be controlled by a user before applying it to an imaging process. The decision data can be generated by the decision engine, and the suggested set of imaging parameter values by a parameter setting engine, wherein both engines may also be formed by one combined engine.

The main input of the parameter setting engine is the decision data generated by the decision engine. In the case the decision indicates that a follow-up scan is necessary or advantageous, the parameter setting engine will generate a second set of values, the suggested set of imaging parameter values, which can then be set for further recording the number of images (e.g., a second scan) with a medical imaging system (a "follow-up scan").

The parameter setting engine can generate the suggested set of imaging parameter values based on the decision data as an input. For example, if the decision data indicates what kind of diagnostic goal should be pursued by the follow-up scan, i.e., which medical condition, which is suspected based on the number of clinical findings, should be the target of the follow-up scan. The parameter setting engine may generate suggested set of imaging parameter values, which are suitable for pursuing the specific diagnostic goal indicated by the decision.

The parameter setting engine may comprise a (deep) neural network. The training of the parameter setting engine may be performed similar to the training of the decision engine, the training of the parameter setting engine may be performed based on an analysis of previously-performed imaging studies. In case of the scan parameter setting engine, it makes sense to take only imaging studies into consideration, in which a follow-up scan has been performed.

Suitable training data to be gathered could e.g. comprise the following information solely or in combination:
- an initial set of imaging parameter values used in the imaging studies used for training;
- the number of clinical findings found in the imaging studies used for training;
- a diagnostic goal to be pursued in the follow-up scan of the imaging studies used for training; and
- a suggested set of imaging parameter values set for a follow-up scan in the imaging studies used for training.

A parameter setting engine and a decision setting engine may be implemented separately from another (e.g., as separate neural networks) or be formed as a combined engine (e.g. as one single neural network). For example, the decision engine may comprise a neural network configured to generate decision data from the number of clinical findings, and the parameter setting engine may be a following neural network configured to generate a suggested set of imaging parameter values from the decision data. In another example, there is one single neuronal network configured to generate decision data and the suggested set of imaging parameter values.

Concerning the separate implementation of the decision engine and the parameter setting engine, the parameter setting engine takes the outputs of the decision engine as inputs and processes them to generate the suggested set of imaging parameter values. Concerning the combined implementation of the decision engine and the scan parameter setting engine, a combined engine (including the functionality of the decision engine and the scan parameter setting engine) is employed.

The combined engine takes the number of clinical findings as an input and processes them to generate the suggested set of imaging parameter values. Optionally, the combined engine can take the initial set of imaging parameter values as an input, also.

A decision module in an embodiment comprises information about a number of clinical guidelines in a memory or in form of a trained decision engine, selection module, or guideline module. This information may be stored in a memory device or in form of training of a neuronal network with this number of clinical guidelines.

A decision module in an embodiment is distributed directly to a medical imaging system, e.g. an MRI system or a CT system.

A decision module in an embodiment is configured as an edge computing application in a network or as a cloud computing application. This means that the decision module is a cloud-based or an edge-based tool.

Edge computing (or fog computing) is any suitable type of application outside a cloud that occurs at the edge of a network. Edge computing mainly uses servers in proximity to the user. In practice, this means that the decision module is located in an intranet, e.g. on the premises of a hospital the examination has been acquired. Edge computing has the advantage that data transfer of large data (e.g. imaging data) via the internet can be avoided.

In an embodiment according to the disclosure, components are part of a data network, wherein the data network and a medical imaging system (i.e., the magnetic resonance imaging system which provides image data) are in data-communication with each other, wherein the data network may e.g. comprise parts of the internet and/or a cloud-based computing system, wherein e.g. a number of components of the disclosure is realized in this cloud-based computing system. For example, the components of the system may be part of a data network, wherein e.g. the data network and a medical imaging system which provides the image data are in communication with each other. Such a networked solution could be implemented via an internet platform and/or in a cloud-based computing system.

The method may also include elements of "cloud computing." In the technical field of "cloud computing," an IT infrastructure is provided over a data network, e.g., a storage space or processing power and/or application software. The communication between the user and the "cloud" is achieved by means of data interfaces and/or data transmission protocols.

In the context of "cloud computing," in an embodiment of the method according to the disclosure, provision of data via a data channel (for example a data network) to a "cloud" takes place. This "cloud" includes a (remote) computing system, e.g., a computer cluster that typically does not include the user's local machine. This cloud may be made available e.g. by the medical facility, which also provides the medical imaging systems. For instance, the image acquisition data is sent to a (remote) computer system (the "cloud") via a RIS (Radiology Information System) or a PACS (Picture Archiving and Communication System).

Within the scope of an embodiment of the disclosure, the abovementioned components (e.g. the "engines") are wholly or partially present on the "cloud" side. An embodiment further comprises a local computing unit connected to the system via a data channel (e.g., a data network, e.g. configured as RIS or PACS). The local computing unit may comprise at least one data receiving interface configured to receive data. Moreover, the local computer may e.g. additionally have a transmission interface to transmit data to the system.

A main advantage of the disclosure is the combination of decision support for determining a possible second diagnostic exam based on imaging data of a first exam with the clinical context of a patient given as his position in the guidelines.

Other objects and features of the present disclosure will become apparent from the following detailed descriptions considered in conjunction with the accompanying drawings. It is to be understood, however, that the drawings are designed solely for the purposes of illustration and not as a definition of the limits of the disclosure.

DETAILED DESCRIPTION

In the diagrams, like numbers refer to like objects throughout. Objects in the diagrams are not necessarily drawn to scale.

Figure 1:
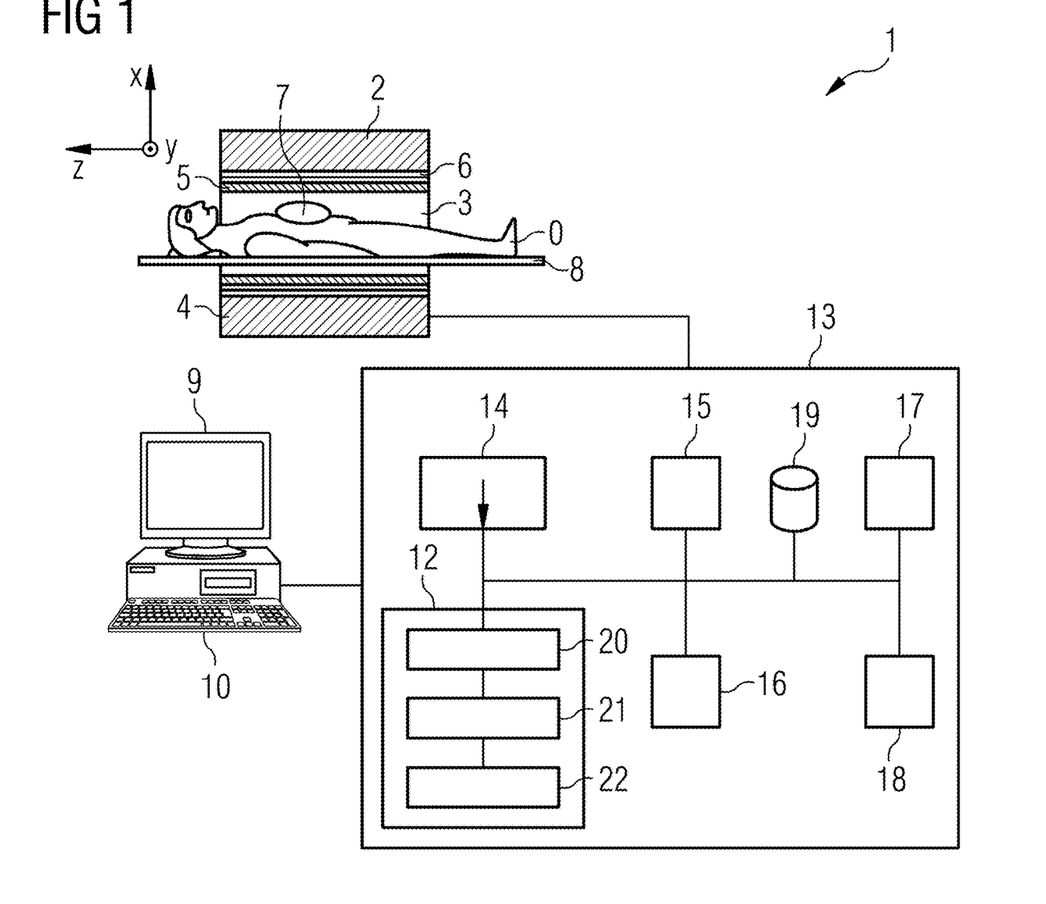
FIG. 1 shows an example MRI system according to an embodiment of the disclosure.

FIG. 1 shows a schematic representation of a magnetic resonance imaging system 1 ("MRI-system") as an example for a medical imaging system. The MRI system 1 includes the actual magnetic resonance scanner (data acquisition unit) 2 with an examination space 3 or patient tunnel in which a patient or test person is positioned on a driven bed 8, in whose body the actual examination object is located.

The magnetic resonance scanner 2 is typically equipped with a basic field magnet system 4, a gradient system 6, as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is configured such that images can be recorded. The basic field magnet system 4 is configured in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils to be able to switch (activate) gradients in the x-direction, y-direction, or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central control device 13 that is used to control the MRI system 1. This central control device 13 includes a sequence control unit 14 for measurement sequence control. With this sequence control unit 14, the series of radio-frequency pulses (RF pulses) and gradient pulses can be controlled depending on a selected pulse sequence within a measurement session. For example, such a series of pulse sequence can be predetermined within a measurement or control protocol. Different control protocols for different measurements or measurement sessions are typically stored in a memory 19 and can be selected by and operator (and possibly modified as necessary) and then be used to implement the measurement.

To output the individual RF pulses of a pulse sequence, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) to acquire magnetic resonance signals (i.e., raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit 9, and measurements can be planned and started by means of the input unit (possibly in combination with the display unit 9), and e.g. suitable control protocols can be selected (and possibly modified) with suitable series of pulse sequence as explained above.

The control device 13 comprises a clinical decision system 12 configured to perform the method according to the disclosure. This clinical decision system 12 comprises the following components that are referred to herein as modules or software modules (see also the following figures describing the function of the components). These modules may thus be implemented as software (e.g. instructions executable via a processor, processing circuitry, etc.), as hardware dedicated components (e.g. an application specific integrated circuit (ASIC), a field programmable gate array (FPGA), etc., or combinations of software and hardware components, in various embodiments.

A data interface 20 is configured to receive initial imaging data D1 from a preceding examination of a patient, and position data PD defining a position L of the patient in a predefined clinical guideline G, and in this example also for outputting the decision data DD.

A CAD engine 21 is configured to determine a number of clinical findings F by automated processing of the initial imaging data D1.

A decision module 22 configured to generate decision data DD based on the determined number of clinical findings F, the position L data PD, and the structure of the clinical guideline G.

It should be noted that neither the decision system 12 nor the single components 21 (CAD engine) and 22 (decision module) are necessarily a part of the unit 13 controlling the scanner. The shown configuration is one possible example. The components can e.g. also be on a separate entity being independent of the scanner on premises or even on a remote server and/or in a cloud.

It should also be noted that the CAD engine 21 and the decision module 22 are not necessarily integrated into the same hardware system. The shown configuration is also one possible example.

The CAD engine 21 and the decision module 22 can be implemented as software and/or hardware as already explained above, e.g. on a processor, processing circuitry, etc.

The MRI system 1 according to the disclosure, and e.g. the control device 13, can have any suitable number of additional components that are not shown in detail but are typically present at such systems, for example a network interface configured to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is generally known to those skilled in the art and thus need not be explained in detail herein.

Figure 2:
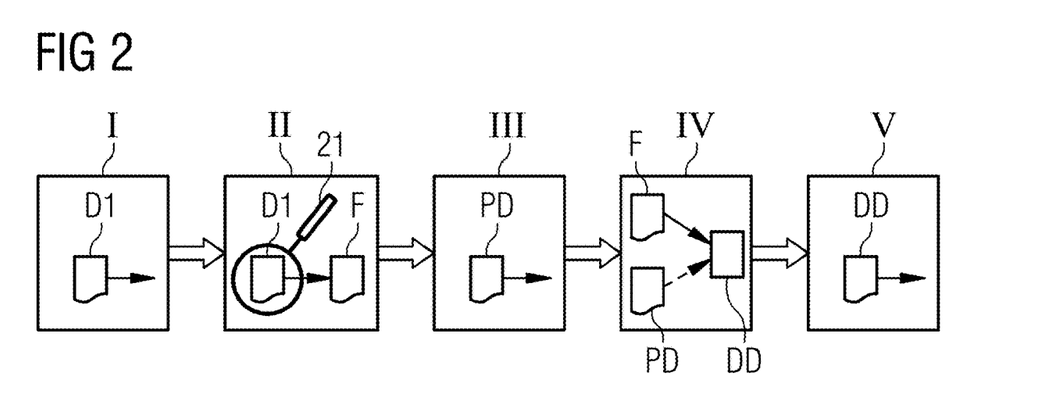
FIG. 2 shows an example block diagram of the process flow of a method according to the disclosure.

FIG. 2 shows a block diagram of the process flow of a preferred method according to the disclosure for image-based operational decision support.

In step I, initial imaging data D1 from a preceding examination of a patient is provided.

In step II, a number of clinical findings F are determined by automated processing of the initial imaging data D1.

In step III, position data PD defining a position L (location L) of the patient in a predefined clinical guideline G (see e.g., FIG. 4) is provided. It should be noted that step III need not necessarily be executed after step I and step II, but may also be executed before or in parallel.

In step IV, decision data DD is generated based on the determined number of clinical findings F, the position data PD, and the structure of the clinical guideline G, with a decision module 22 (see FIG. 1). The decision data DD at least comprises information indicating which next steps S1, S2, S3 (see FIG. 4) from a set of possible next steps S1, S2, S3 of the clinical guideline G originating from the actual position L of the patient should be performed.

In step V, the decision data DD is outputted, which can comprise displaying, transmitting, and/or storing the decision data DD.

Figure 3:
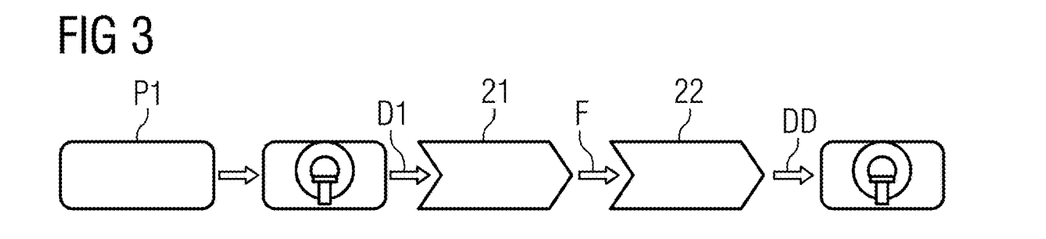
FIG. 3 shows an example of a test-algorithm chain according to an embodiment of the disclosure.

FIG. 3 shows an example of a test-algorithm chain according to an embodiment of the disclosure. From left to right, an initial set of imaging parameter values P1 is provided for a first scan procedure (symbolized by an MRI scanner) producing an initial set of imaging data DE This initial imaging data D1 is then examined for a number of clinical findings F by a CAD engine 21 that are further used by a decision module 22 to produce decision data DD indicating a following scan procedure (right box) or other diagnostic procedures (e.g., laboratory diagnostic tests).

Figure 4:
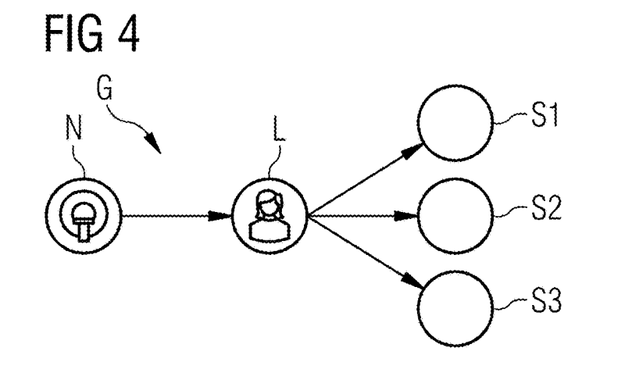
FIG. 4 shows a part of an example guideline according to an embodiment of the disclosure.

FIG. 4 shows a part of a guideline G corresponding to a decision problem that can be supported based on the proposed disclosure. In this embodiment, the guideline G corresponds to a standardized procedure a medical practitioner or a group of medical practitioners follows in the treatment of a certain disease (e.g., lung cancer or prostate cancer). In this embodiment, the standardized procedure was defined by a standardization body, alternatively, the standardized procedure could be hospital specific (in this case, one could denote the guideline G as "standard operating procedure"). The guideline G comprises nodes L, S1, S2, S3 and directed edges between the nodes L, S1, S2, S3. The nodes L1, S1, S2, S3 can correspond to different stages or steps of a patient within the guideline G, for example a diagnostic step, a therapeutic step, a decision step, or the like. The directed edges encode the potential order of stages or steps of the patient according to the guideline. Based on the additional patient data, the patient can be located in the guideline G to be at a decision node (location L) after a diagnostic step corresponding to the first imaging examination (left node N with the symbolized MRI scanner). The possible outcomes (steps S1 S2 S3), e.g., "no further diagnostic" in the upper step S1 or "further diagnostic procedure 1" in the middle step S2 or "further diagnostic procedure 2" in the lower step S3 are restricted by the number of possible next steps S1, S2, S3 originating from the location L of the patient within the guideline G.

Based on the outcome of the initial imaging examination, the next step S1, S2, S3 in the clinical pathway of the patient can be selected from the three options shown.

For the decision module 22 described above, this means that, based on the location L of the patient in the clinical guide-lines G, it is known before the execution of the decision engine 22 that there are only three possible outcomes of the decision module 22, e.g.:
 no further diagnostics needed (corresponding to the upper step S1);
 additional diagnostic procedure 1 needed (e.g., a CT scan with a first protocol), corresponding to step S2; or
 additional diagnostic procedure 2 needed (e.g., a MR scan with a second protocol), corresponding to step S3.

Figure 5:
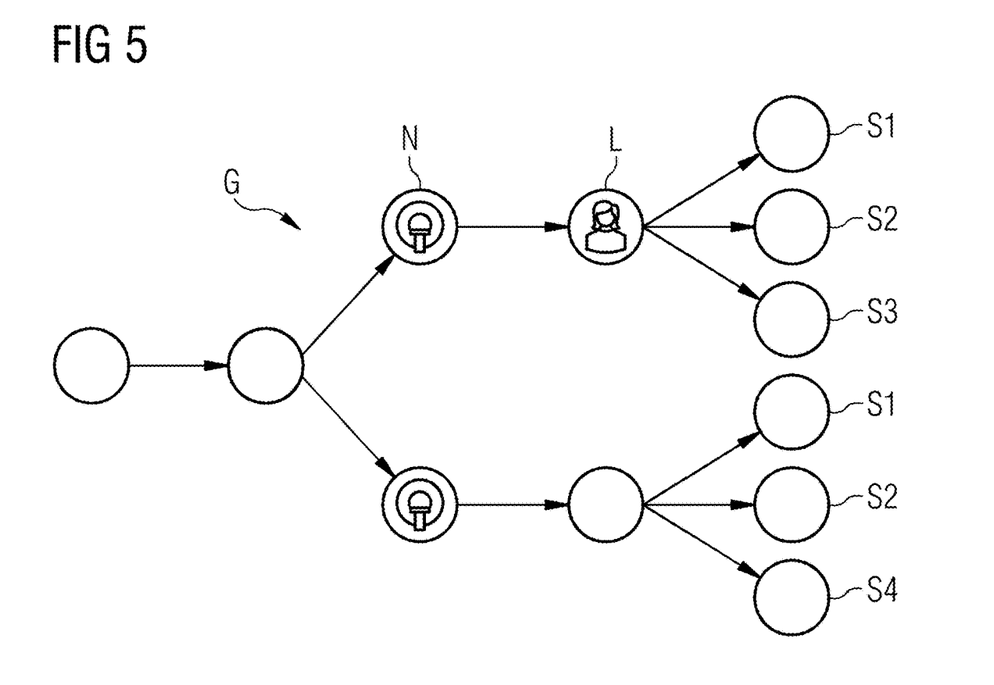
FIG. 5 shows an extended part of an example guideline according to an embodiment of the disclosure.

FIG. 5 shows an extended part of a guideline G corresponding to a decision problem that can be supported based on the proposed disclosure. This clinical guideline G could be a standard operating procedure SOP, and illustrates that the exact same first imaging examination can be executed at different locations L of the guideline G, and for every location L, the possible next steps S1, S2, S3 (and so the possible outcomes of the decision engine) can be different.

For example, the earlier diagnostic step in this case (left) can be the decision whether the patient is eligible for an MRI (e.g., not having a metal implant). For the upper branch of the guideline G, the same options (possible outputs of the decision engine) as in FIG. 4 are applicable:
 No further diagnostics needed (corresponding to step S1);
 Additional diagnostic procedure 1 needed (e.g., a CT scan with the first protocol; corresponding to step S2); or
 Additional diagnostic procedure 2 needed (e.g., a MR scan with the second protocol; corresponding to step S3);

In contrast, in the lower branch, there could be the following possible next steps, because the patient is not eligible for a MRI examination:
 No further diagnostics needed (corresponding to step S1);
 Additional diagnostic procedure 1 needed (e.g., a CT scan with the first protocol; corresponding to step S2); or
 Additional diagnostic procedure 3 needed (e.g., a CT scan with a third protocol; corresponding to step S4).

Figure 6:
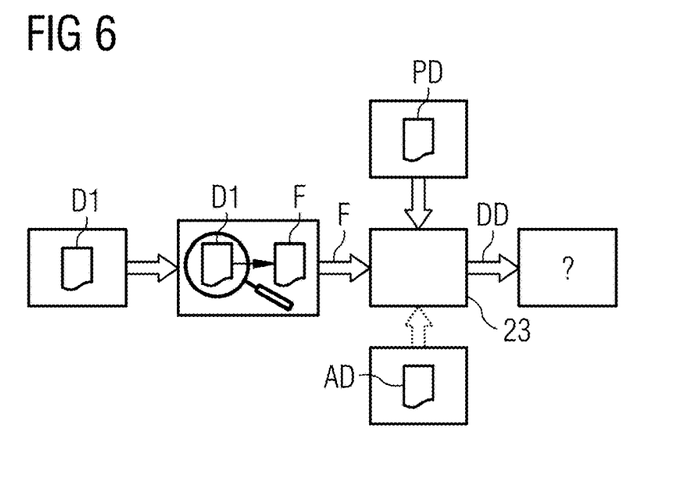
FIG. 6 shows an example trained decision engine according to an embodiment of the disclosure.

FIG. 6 shows an embodiment of the disclosure with a trained decision engine 23. Here, the number of clinical findings F, as well as position data PD and optionally also additional patient data AD, are inputted in the decision engine 23. The decision engine 23 then generates decision data DD based on the input data. Looking at FIG. 4, the position data PD indicating that the patient is localized as shown in FIG. 4, the decision engine 23 will produce decision data only with respect to the three possible steps S1, S2, S3.

Here and in the following figures, the arrow-shaped boxes may represent the clinical decision system (with additional data interfaces for inputs and outputs).

Figure 7:
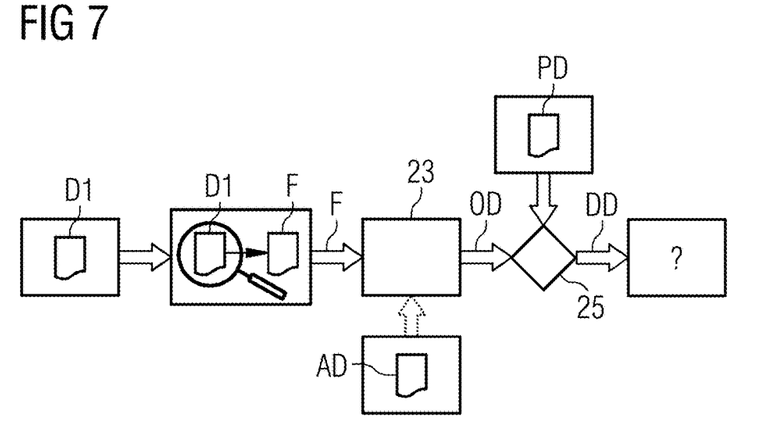
FIG. 7 shows an example a decision engine and a guideline module according to an embodiment of the disclosure.

FIG. 7 shows an embodiment of the disclosure with a decision engine 23 and a guideline module 25. In contrast to FIG. 6, this embodiment does not need a specially trained decision engine 23. The possible steps S1, S2, S3 (see e.g., FIG. 4) are limited by the succeeding guideline module 25 narrowing the possible steps S1, S2, S3 provided by the decision engine 23 to those possible from the location L in the clinical guideline G.

Figure 8:
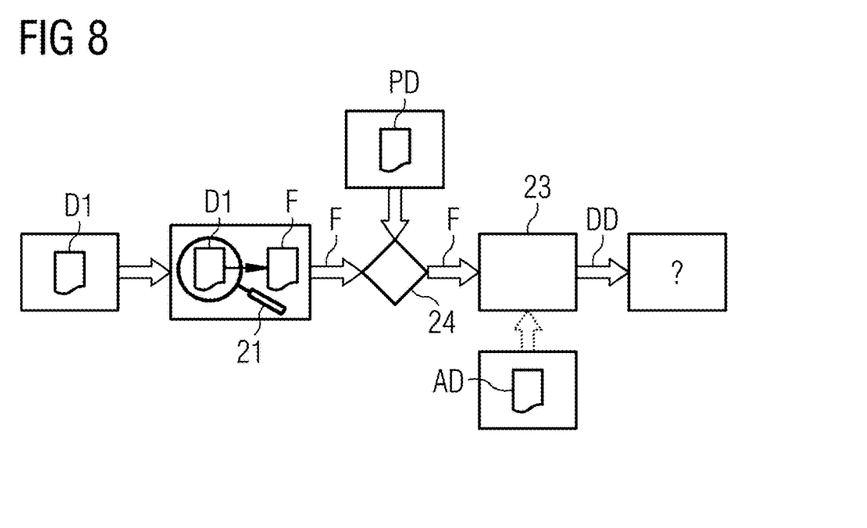
FIG. 8 shows an example decision engine and selection module according to an embodiment of the disclosure.

FIG. 8 shows an embodiment of the disclosure with a decision engine 23 and a selection module 24. In contrast to FIGS. 6 and 7, this embodiment has specially trained decision engines 23 for different locations L in the clinical guideline G. The matching decision engine 23 is chosen by the selection module 24 based on the position data PD and receives the number of clinical findings F of the CAD engine 21.

Figure 9:
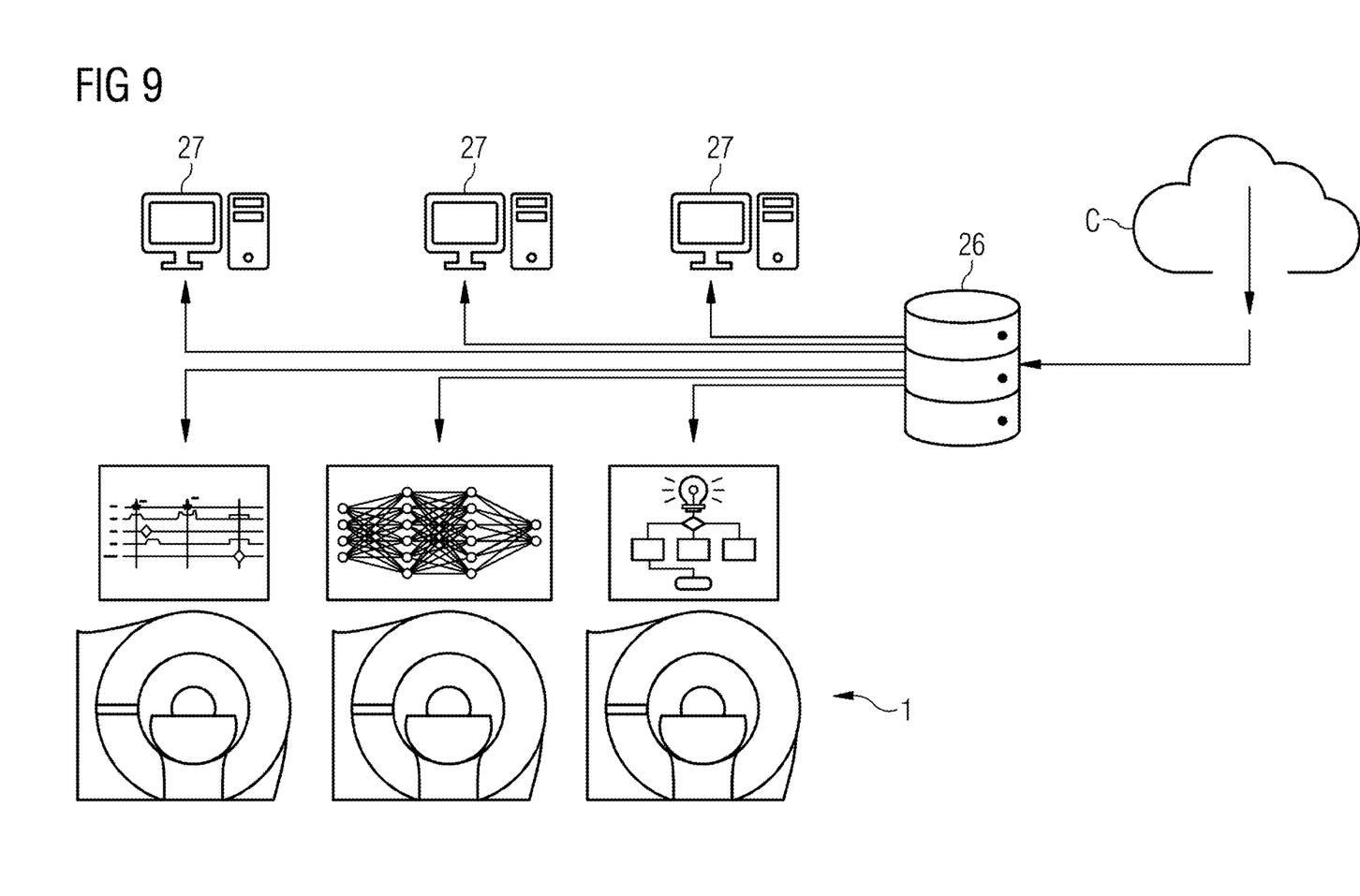
FIG. 9 shows an example setup according to an embodiment of the disclosure.

FIG. 9 shows an embodiment of an example setup of the disclosure and specifies how the decision engine and/or the clinical guidelines G can be distributed in an edge-like setting. The other figures should be consulted for the design of the single components.

In an embodiment of the disclosure, the decision engine 23 (and also the CAD engine) may be operated on a cloud platform C. However, it is also possible to have the decision engine 23 on the edge, meaning that they are stored and executed in the hospital itself (either on a dedicated server 26 within the hospital, or directly on the medical imaging machine), but are distributed and/or managed centrally from the cloud platform C.

An advantage in this case is that the imaging data does not leave the premises of the hospital, which might be required from a data privacy perspective and can lead to a decrease of the throughput time, because the medical images do not have to be transferred via the internet.

In one embodiment, the decision engine 23 may be a cloud-based tool (here present in the cloud platform C). However, the decision engine 23 may also be an edge-based tool in the server 26, because then data transfer of large data (e.g. imaging data) via the internet can be avoided. In another advantageous embodiment, the decision engine 23 can be distributed directly to a medical imaging scanner (e.g., as shown in FIG. 1).

This figure shows two alternatives that may be selected separately or in combination. The first alternative is a distribution to several MRT systems 1, and the second alternative is the distribution to several workstations 27.

The server 26 (e.g., used as customer repository) is optional, but can be used to adopt the decision engine and/or the underlying guidelines on the hospital level. For example, a standard version is provided in the cloud platform C by the 3rd party repository, adapted and stored in the customer repository (the server 26), and then centrally distributed.

Although the present disclosure has been disclosed in the form of preferred embodiments and variations thereon, it will be understood that numerous additional modifications and variations could be made thereto without departing from the scope of the disclosure. For the sake of clarity, it is to be under-stood that the use of "a" or "an" throughout this application does not exclude a plurality, the expression "a number of" means "at least one," and "comprising" does not exclude other steps or elements. The mention of a "unit" or a "device'" does not preclude the use of more than one unit or device.

The various components described herein may be referred to as "units" or "modules." Such components may be implemented via any suitable combination of hardware and/or software components as applicable and/or known to achieve the intended respective functionality. This may include mechanical and/or electrical components, processors, processing circuitry, or other suitable hardware components configured to execute instructions or computer programs that are stored on a suitable computer readable medium. Regardless of the particular implementation, such devices and units, as applicable and relevant, may alternatively be referred to herein as "circuitry," "processors," or "processing circuitry".

What is claimed is:

1. A decision engine configured to provide image-based operational decision support, comprising:
    a memory configured to store instructions; and
    processing circuitry configured to execute the instructions stored in the memory to:
        generate output data based on a predetermined number of clinical findings in medical images of a patient; and
        perform, based upon a trained module that is trained in accordance with training data, post-processing of the output data to generate decision data depending on position data defining a current position of the patient in a predefined clinical guideline comprising a set of possible next steps subsequent to the current position within the predefined clinical guideline,
    wherein the decision data comprises information indicating which steps from among the set of possible next steps of the predefined clinical guideline should be performed.

2. The decision engine according to claim 1, wherein the decision engine is trained on a predetermined number of training clinical findings and position data of a reference patient to generate the decision data as output data, and
    wherein the output data comprises information indicating which steps from among the set of possible next steps of the predefined clinical guideline should be performed depending on the position data of the reference patient.

3. The decision engine according to claim 1, wherein the memory is configured to store further instructions that, when executed by the processing circuitry, cause the processing circuitry to function as the trained module to perform the post-processing of the output data, and to generate the decision data by selecting the output data depending on the position data and the next steps of the predefined clinical guideline with respect to the current position of the patient within the predefined clinical guideline.

4. The decision engine according to claim 3, wherein the training data comprises multiple sets of output data of the decision engine, a number of training clinical guidelines, and position data of a reference patient, to generate the decision data, and
    wherein a ground truth within the training data comprises information indicating which next step from among a set of possible next steps of a training clinical guideline subsequent to a current position of the reference patient as indicated by the position data of the reference patient.

5. The decision engine according to claim 1, wherein the memory is configured to store further instructions that, when executed by the processing circuitry, cause the processing circuitry to function as a selection module to select a decision engine from among a number of trained decision engines based on the position data.

6. The decision engine according to claim 5, wherein each of the number of trained decision engines is trained based on respective training data to generate respective decision data as respective output data, the respective training data used to train each one of the number of trained decision engines comprising (i) a determined number of clinical findings of a reference patient, and (ii) a ground truth comprising information indicating which next step from among a set of possible next steps of a training clinical guideline subsequent to a current position indicated by position data of a reference patient.

7. The decision engine according to claim 1, wherein the processing circuitry is configured to execute the instructions stored in the memory to generate the decision data further depending on predefined additional patient data including an age of the patient, a weight of the patient, a size of the patient, a sex of the patient, health conditions of the patient, known co-morbidities of the patient, laboratory results of the patient, and/or prior imaging results of the patient.

8. The decision engine according to claim 1, wherein the processing circuitry is configured to execute the instructions stored in the memory to additionally generate information in a form of the output data or the decision data about one or more of a modality to be used for a further imaging examination, an imaging protocol to be used, and/or scheduling of a further imaging examination.

9. The decision engine according to claim 1, wherein the processing circuitry is configured to execute the instructions stored in the memory to additionally output a suggested set of imaging parameter values for recording an image of the patient in the course of a further imaging examination.

10. A computer-implemented method for image-based operational decision support, comprising:
    generating initial imaging data from a preceding examination of a patient;
    determining, via automated processing of the initial imaging data, a number of clinical findings in medical images of a patient by:
        providing position data defining a current position of the patient within a predefined clinical guideline; and
        performing, based upon a trained module that is trained in accordance with training data, post-processing of the determined number of clinical findings to generate decision, the position data, and a structure of the predefined clinical guideline comprising a set of possible next steps subsequent to the current position of the patient in the predefined clinical guideline, the decision data comprising information indicating which steps from among the set of possible next steps of the predefined clinical guideline should be performed; and
    outputting the decision data.

11. The method according to claim 10, further comprising:
    determining, based on patient data, the position data providing the current position of the patient within the predefined clinical guideline.

12. A clinical decision system for image-based operational decision support, comprising:
a data interface configured to receive (i) initial imaging data from a preceding examination of a patient, and (ii) position data defining a current position of the patient in a predefined clinical guideline; and
processing circuitry configured to:
determine a number of clinical findings via automated processing of the initial imaging data; and
perform, based upon a trained module that is trained in accordance with training data, post-processing of the determined number of clinical findings to generate decision data, the position data, and a structure of the predefined clinical guideline,
wherein the data interface is further configured to output the decision data.

13. The clinical decision system of claim 12, wherein the clinical decision system is part of a medical imaging system configured to record images of the patient in the form of imaging data.

14. The decision engine according to claim 1, wherein the training data comprises a dataset that functions to restrict the decision data to next steps within the predefined clinical guideline.

15. The decision engine according to claim 1, wherein a ground truth within the training data comprises information indicating which next step from among a set of possible next steps of a training clinical guideline subsequent to a current position of a reference patient as indicated by position data of the reference patient.

16. The decision engine according to claim 1, wherein the memory is configured to store further instructions that, when executed by the processing circuitry, cause the processing circuitry to function as a selection module to select a decision engine that is trained on the training data to generate the decision data as the output data, and wherein the training data comprises a determined number of clinical findings of a reference patient.

17. The decision engine according to claim 16, wherein the training data further comprises a ground truth comprising information indicating which next step from among a set of possible next steps of a training clinical guideline subsequent to a current position indicated by position data of the reference patient.

18. The decision engine according to claim 1, wherein the training data functions to restrict the decision data to next steps within the predefined clinical guideline, which is associated with a medical facility at which the medical images of the patient were acquired.

19. The decision engine according to claim 1, wherein the memory is configured to store further instructions that, when executed by the processing circuitry, cause the processing circuitry to restrict the decision data such that the steps from among the set of possible next steps of the predefined clinical guideline are associated only with diagnostic goals achieved via respective imaging modalities.

* * * * *